US00PP18457P2

(12) United States Plant Patent
Gutter

(10) Patent No.: US PP18,457 P2
(45) Date of Patent: Jan. 22, 2008

(54) *AUBRIETA* PLANT NAMED 'AUDELPUR'

(50) Latin Name: *Aubrieta hybrida*
Varietal Denomination: Audelpur

(75) Inventor: Martien Gutter, Enkhuizen (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/486,308

(22) Filed: Jul. 13, 2006

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

| | | | |
|---|---|---|---|
| 4,636,950 | A | 1/1987 | Caswell et al. |
| 5,478,989 | A | 12/1995 | Shepley |
| 5,532,928 | A | 7/1996 | Stanczyk et al. |
| 5,699,525 | A | 12/1997 | Embutsu et al. |
| 5,712,989 | A | 1/1998 | Johnson et al. |
| 5,841,115 | A | 11/1998 | Shepley |
| 5,914,472 | A | 6/1999 | Foladare et al. |
| 5,960,402 | A | 9/1999 | Embutsu et al. |
| 5,965,858 | A | 10/1999 | Suzuki et al. |
| 5,979,240 | A | 11/1999 | Rix et al. |
| 6,024,281 | A | 2/2000 | Shepley |
| 6,047,843 | A | 4/2000 | Mecke |
| 6,131,744 | A | 10/2000 | Pratt |
| 6,378,721 | B1 | 4/2002 | Williams |
| 6,386,386 | B1 | 5/2002 | George |
| 6,425,487 | B1 | 7/2002 | Emmott et al. |
| 6,530,518 | B1 | 3/2003 | Krichilsky et al. |
| 6,643,624 | B2 | 11/2003 | Philippe et al. |
| 2002/0016731 | A1 | 2/2002 | Kupersmit et al. |
| 2002/0059175 | A1 | 5/2002 | Nakano |
| 2002/0120502 | A1 | 8/2002 | Sakaguchi |

OTHER PUBLICATIONS

PBR 06–5689—filed Dec. 7, 2006.*
PBR 20051045—date published Aug. 15, 2005.*
Article: Dietitian/Healthy Eating Services "Transforming How Dietitions Offer Advice"; AirClic; 2001–2003.
Article: Shop Smart, Eat Right "Healthier, More Nutritious Meals"; Beeline Shopper; 2001–2003.
Article: Shop Smart, Eat Right—Sample Grocery List "Guide Yourself to Healthier Eating"; Beeline Shopper; 2001–2002.
Article: Shop Smart, Eat Right—Sample Recipes "Great Meats Made Easy"; Beeline Shopper; 2001–2002.

* cited by examiner

*Primary Examiner*—Wendy C. Haas
*Assistant Examiner*—Georgia Helmer
(74) *Attorney, Agent, or Firm*—Bruce Vrana

(57) ABSTRACT

A new *Aubrieta* plant, characterized particularly as to novelty by the purple flowers, the early flowering and the strong dentation of the leaves.

1 Drawing Sheet

Latin name of the genus and species of the plant claimed: *Aubrieta hybrida.*
Varietal denomination: 'Audelpur'.

BACKGROUND OF THE NEW PLANT

The present invention comprises a new distinct cultivar of *Aubrieta,* botanically known as *Aubrieta hybrida.*

The new *Aubrieta* is a product of a planned breeding program conducted in Enkhuizen, Netherlands. The new *Aubrieta* cultivar has a compact growth habit and an early flowering in several colors.

The present cultivar originates from a cross-pollination made in 1998, of a proprietary *Aubrieta* selection identified as 'A002,' not patented, as the female, or seed parent, with a proprietary *Aubrieta* selection identified as 'A009,' not patented, as the male, or pollen parent. A seedling from this cross was selected in 1999.

The present cultivar has been repeatedly asexually reproduced by cuttings in Enkhuizen, Netherlands, in Angers, France, in Gilroy, USA since 1999. The distinctive characteristics of this new *Aubrieta* are stable and reproduced true to type in successive generations of asexual reproduction. It takes 25 to 29 weeks to produce a finished plant, depending on the temperature.

This new *Aubrieta* plant is a perennial in all climatic zones in the US.

DESCRIPTION OF THE DRAWING

This new *Aubrieta* plant is illustrated by the accompanying photographic drawing of a 28 week old plant which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new *Aubrieta.* The data which defines these characteristics were collected from asexual reproductions carried out in Enkhuizen, Netherlands. The plant history was taken on 35 week old plants, blossomed under natural light in the field.

Color readings were taken in the office under ambient light. Color references are primarily to The R.H.S. Colour Chart of The Royal Horticultural Society of London.

Plants of the new *Aubrieta* differ primarily from the plants of the female parent selection in the following characteristics:

Plants of the new variety have purple flowers and a compact growth habit, whereas plants of the female parent selection have red flowers and a very loose growth habit.

Plants of the new *Aubrieta* differ primarily from the plants of the male parent selection in the following characteristics:

Plants of the new variety have purple flowers and an early flowering, whereas plants of the male parent selection have mid blue flowers and a late flowering.

TABLE 1

DIFFERENCES BETWEEN THE NEW CULTIVAR 'AUDELPUR' AND A SIMILAR CULTIVAR

| | 'Audelpur' | 'Purple Supreme' (not patented) |
|---|---|---|
| Earliness | Early | Late |
| Leaf margin | More pronounced dentate | Less pronounced dentate |

Parentage:
*Female parent.*—'A002,' not patented.
*Male parent.*—'A009,' not patented.
Propagation:
*Type cutting.*—Terminal cuttings.
*Time to initiate roots.*—12-14 days at 18° C.
*Time to produce a rooted cutting.*—5 weeks.
*Root description.*—Fine, fibrous and white in color.
Plant description:
*General appearance.*—Makes long branches that tend to grow decumbent.
*Growth and branching habit.*—Freely branching habit, freely flowering. Vigorous.
*Plant height.*—5 cm.
*Plant spread.*—30 cm.
Lateral branches:
*Length.*—Primary branch: 12-17 cm. Secondary branch: 5-10 cm.
*Diameter.*—0.15 cm.
*Texture.*—Smooth, pubescent.
*Internode length.*—0.5-3 cm.
*Color.*—RHS 144B.
Foliage description:
*Arrangement.*—Alternate.
*Length, mature leaves.*—2 cm.
*Width, mature leaves.*—0.7 cm.
*Shape.*—Oblanceolate.
*Apex.*—Acute.
*Base.*—Attenuate.
*Margin.*—Dentate. 2-4 dents per leaf.
*Texture.*—Smooth, pubescent.
*Venation pattern.*—Pinnate. Veins are hardly visible.
*Color young foliage, upper surface.*—RHS 137A.
*Color young foliage, lower surface.*—RHS 138B.
*Fully expanded foliage, upper surface.*—RHS 137A.
*Fully expanded foliage, lower surface.*—RHS 138B.
*Venation, upper surface.*—RHS 142B.
*Venation, lower surface.*—RHS 142B.
*Petiole.*—Absent.
Flower description:
*Flower type.*—Single, cruciform.
*Number of flowers and flower buds per lateral branch.*—3-15.
*Flower position.*—At top of branch.
*Fragrance.*—Absent.
*Flowering season.*—Spring.
*Flower diameter.*—1.5-2 cm.
Flower buds:
*Bud length* (*at stage of showing color*).—0.7 cm.
*Bud diameter.*—0.4 cm.
*Bud shape.*—Ovate.
*Texture.*—Smooth, pubescent.
*Color, just before opening.*—Base: RHS 145A. Apex: RHS 137A with anthocyanin.
Petals:
*Shape.*—Petal has an elliptic base and an orbicular apex.
*Quantity.*—4 per flower, imbricate.
*Petal base length.*—0.8 cm.
*Petal base width.*—0.2 cm.
*Petal base margin.*—Entire.
*Petal base texture.*—Smooth.
*Petal base color.*—Upper surface: RHS 1C. Lower surface: RHS 1C.
*Petal apex length.*—0.7 cm.
*Petal apex width.*—0.8 cm.
*Petal apex margin.*—Entire.
*Petal apex texture.*—Smooth.
*Petal apex color.*—Upper surface: RHS N81A. Lower surface: RHS N81B.
Sepals:
*Quantity.*—4 per flower.
*Shape.*—Elliptic.
*Apex.*—Acute.
*Margin.*—Entire.
*Length.*—0.8 cm.
*Width.*—0.3 cm.
*Color upper surface.*—Immature: RHS 137A with some anthocyanin. Mature: RHS 137A with very much anthocyanin.
*Color lower surface.*—RHS 138B.
*Texture upper surface.*—Smooth, pubescent.
*Texture lower surface.*—Smooth, glabrous.
Peduncles:
*Length.*—0.7 cm.
*Diameter.*—0.1 cm.
*Color.*—RHS 138A with some anthocyanin.
*Texture.*—Smooth, pubescent.
Reproductive organs:
*Androecium.*—Stamen number: 6, not fused. Filament length: 0.4-0.8 cm. Filament color: RHS 2D. Anther shape: Ovate. Anther length: 0.2 cm. Anther color: RHS 2B. Color of pollen: RHS 2A. Amount of pollen: Normal.
*Gynoecium.*—Pistil number: One. Pistil length: 0.6 cm. Stigma color: RHS 150B. Style color: RHS N144C. Ovary color: RHS 138B.
Seed development: Seed development has not been observed.
Disease/pest resistance: No disease/pest resistance has been observed.

What is claimed is:

1. A new and distinct cultivar of *Aubrieta* plant named 'Audelpur,' as substantially illustrated and described herein.

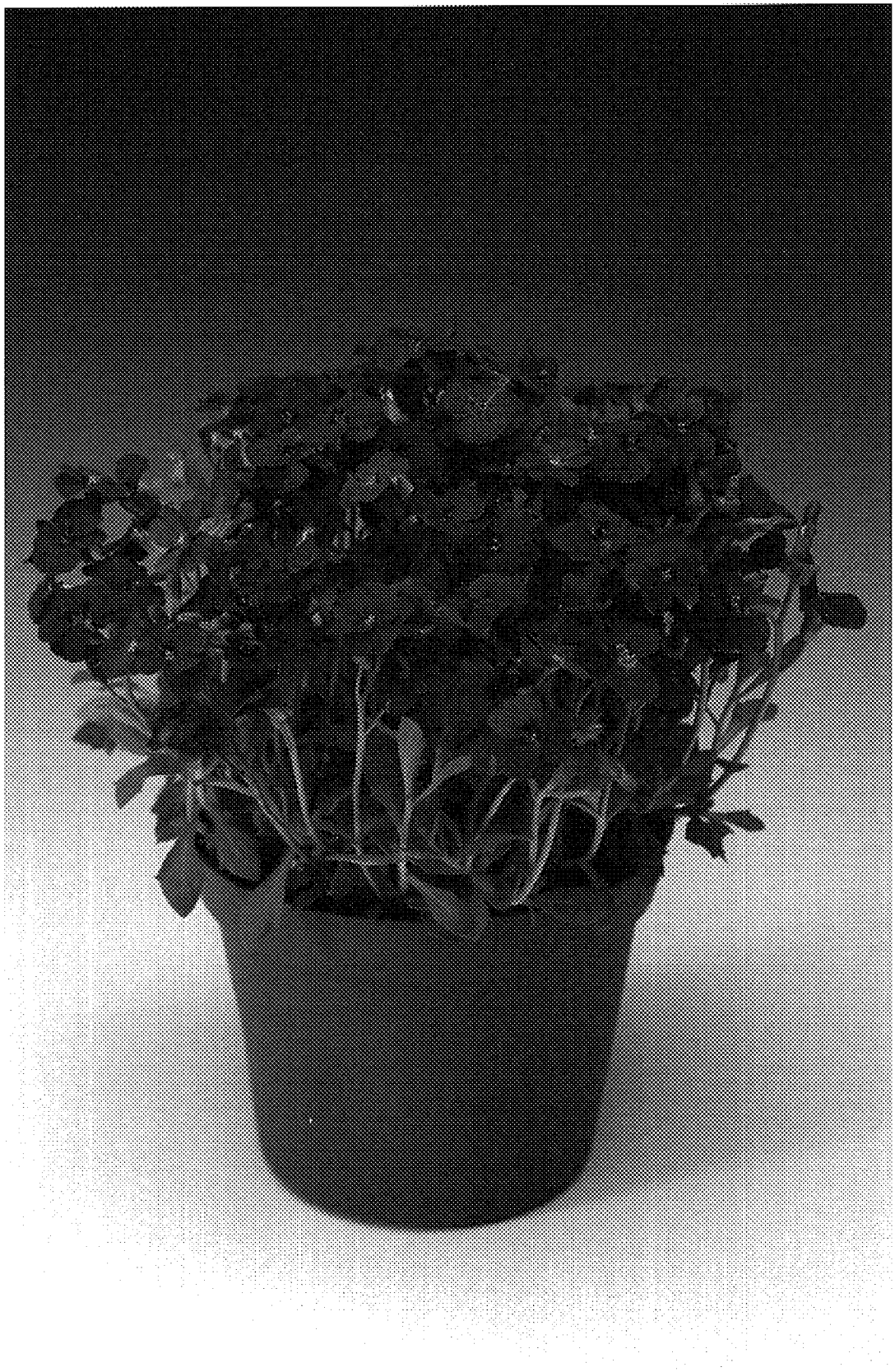

* * * * *